(12) United States Patent
Nakayama et al.

(10) Patent No.: US 6,448,018 B1
(45) Date of Patent: Sep. 10, 2002

(54) FLUORESCENCE POLARIZATION METHOD AT MULTIPLE WAVELENGTHS

(75) Inventors: Hiroshi Nakayama, Hirakata; Fumihisa Kitawaki, Kadoma; Jinsei Miyazaki, Higashiosaka, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/346,817

(22) Filed: Jul. 2, 1999

(30) Foreign Application Priority Data

Jul. 3, 1998 (JP) ............................................ 10-189512

(51) Int. Cl.[7] ........................ G01N 33/53; C09K 11/06; G01J 4/00
(52) U.S. Cl. ................ 435/7.1; 252/301.16; 250/459.1
(58) Field of Search .............................. 435/7.1, 5, 7.2, 435/7.31, 7.32, 7.94, 125; 436/820, 164, 166, 172; 424/9.6; 252/301.16; 250/459.1

(56) References Cited

U.S. PATENT DOCUMENTS

| | | | |
|---|---|---|---|
| 4,902,630 A | | 2/1990 | Bennett et al. ............. 436/546 |
| 4,923,819 A | * | 5/1990 | Fernandez et al. .......... 436/518 |
| 5,132,432 A | * | 7/1992 | Haugland et al. ........... 548/518 |
| 5,166,052 A | | 11/1992 | Cercek et al. ............. 435/7.24 |
| 5,210,015 A | | 5/1993 | Gelfand et al. ................. 435/6 |
| 5,302,349 A | | 4/1994 | Danliker et al. ......... 422/82.08 |
| 5,824,557 A | | 10/1998 | Burke et al. ................. 436/94 |
| 5,994,143 A | * | 11/1999 | Bieniarz et al. ............. 436/91 |
| 6,022,686 A | * | 2/2000 | Garman et al. ................. 435/6 |

FOREIGN PATENT DOCUMENTS

JP          3188374          8/1991

OTHER PUBLICATIONS

Lundblad et al., Fluorescence Polarization Analysis of Protein—Protein Interactions, Molecular Endocrinology (10:607–12), 1996 by the Endocrine Society.*
Chen et al., Fluorecence Decay Times: Protein, Coenzymes, and Other Compounds in Water; Science vol. 156, May 19, 1967; pp. 949–952.*
European Search Report for Application No. EP 99 30 5267, Mar. 11, 2000.

* cited by examiner

*Primary Examiner*—John S. Brusca
(74) *Attorney, Agent, or Firm*—Jacqueline F. Mahoney; Judy M. Mohr; Perkins Coie LLP

(57) ABSTRACT

A method of the present invention is a fluorescence polarization method at multiple wavelengths for analyzing two or more different assay-objects in a sample. The method includes the steps of: (a) providing two or more different fluorescent-labeled substances, each being a substance which is capable of specifically binding to respective one of the assay-objects and is covalently bound to a fluorochrome, wherein the fluorochromes of the fluorescent-labeled substances are different from one another; (b) allowing the fluorescent-labeled substances to bind to the two or more different assay-objects, respectively; and (c) measuring a change in the degree of fluorescence polarization which has taken place in each of the fluorescent-labeled substances by its binding to one of the assay-objects.

14 Claims, 2 Drawing Sheets

Measurement of CG and CRP using fluorescence polarization immunoassay

Measurement of CRP and amyloid A using fluorescence polarization immunoassay at multiple wavelength

FLUORESCENCE POLARIZATION METHOD AT MULTIPLE WAVELENGTHS

BACKGROUND OF THE INVENTION

1. Field of the Invention

The present invention relates to a fluorescence polarization method at multiple wavelengths for analyzing two or more different assay-objects in a sample in one reaction system. The present invention is particularly useful in the fields of art of environmental assay, food control, and medical diagnosis.

2. Description of the Related Art

The fluorescence polarization method is known in the art as a method for assaying a substance in a sample. The method is based on the principle that when a fluorescent-labeled compound is excited by linearly polarized light, the fluorescence emitted from the compound has a degree of polarization which is in proportion to the molecular weight thereof.

As a fluorescence polarization method which has been developed, there is a fluorescence polarization immunoassay based on an antigen-antibody reaction.

For example, U.S. Pat. No. 4,902,630 discloses an assay method in which a body fluid (particularly, a blood) containing CRP, an assay-object, is added to a mixed solution which contains: a "tracer" obtained by binding fluorescein, a fluorochrome, to C-reactive protein (CRP); and an antibody which is capable of specifically binding to CRP. CRP in the sample is assayed based on competition between the tracer and CRP for binding the antibody in the mixed solution.

Japanese Laid-Open Publication No. 3-188374 discloses a method in which a fluorescent-labeled particle comprising an insoluble carrier particle carrying a fluorochrome (or a phosphorescence dye) and an antigen (or an antibody) is reacted with a sample solution containing an antibody (or an antigen). The antibody (or an antigen) in the sample is assayed based on the aggregation of the particles due to an antigen-antibody reaction.

However, the conventional methods are designed to assay only one substance in a sample, and cannot assay two or more different substances in a sample in one reaction system. Accordingly, there has been a demand in the art for development of a method which is suitable for assaying two or more different substances in a sample in one reaction system.

SUMMARY OF THE INVENTION

According to one aspect of this invention, there is provided a fluorescence polarization method at multiple wavelengths for analyzing two or more different assay-objects in a sample. The method includes the steps of: (a) providing two or more different fluorescent-labeled substances, each being a substance which is capable of specifically binding to respective one of the assay-objects and is covalently bound to a fluorochrome, wherein the fluorochromes of the fluorescent-labeled substances are different from one another; (b) allowing the fluorescent-labeled substances to bind to the two or more different assay-objects, respectively; and (c) measuring a change in the degree of fluorescence polarization which has taken place in each of the fluorescent-labeled substances by its binding to one of the assay-objects.

In one embodiment of the invention, each of the two or more different assay-objects is independently a biological substance, a microorganism, a virus, a pharmaceutical, an environmental pollutant or an abused drug.

In one embodiment of the invention, the biological substance is a peptide, a protein, a lipid, a saccharide or a nucleic acid.

In one embodiment of the invention, the protein is an antibody, a hormone, an inflammation marker, a coagulation factor, an apolipoprotein, a high density lipoprotein (HDL), a low density lipoprotein (LDL), a glycosylated albumin, a glycosylated hemoglobin, a hemoglobin, or an enzyme.

In one embodiment of the invention, the hormone is chorionic gonadotropin, thyroid-stimulating hormone, progesterone, follicular forming hormone, parathyroid-stimulating hormone, adrenocorticotropic hormone, or insulin.

In one embodiment of the invention, the inflammation marker is C-reactive protein (CRP), $\alpha$1-antitrypsin ($\alpha$1-AT), $\alpha$l-antichymotrypsin ($\alpha$l-X), $\alpha$l-acid glycoprotein ($\alpha$1-AG), haptoglobin (Hp), ceruloplasmin (Cp), the 9th component of complement (C9), the 4th component of complement (C4), the 3rd component of complement (C3), complement factor B (B), fibrinogen (Fbg), serum amyloid A (SAA), C1 inhibitor (ClI), a sialoglycoprotein, an acid-soluble protein (ASP) or an immunosuppressive acidic protein (IAP).

In one embodiment of the invention, the microorganism is staphylococcus, Sarcina, Spirillum, Steptococcus, coccobacillus, bacillus, Spirochaeta, tetracoccus, comma bacillus, or Actinomyces.

In one embodiment of the invention, the specifically-binding substance is a protein which is a antibody, an antigen, a receptor, or an inhibitor.

In one embodiment of the invention, the antibody is a set of polyclonal antibodies, a monoclonal antibody, a chimeric antibody, a Fab antibody or a (Fab)2 antibody.

In one embodiment of the invention, the fluorochrome has a functional group which is capable of binding to a primary, secondary or tertiary amino group, a carboxyl group, a thiol group, a phenyl group, a phenol group or a hydroxyl group.

In one embodiment of the invention, a lifetime of fluorescence of the fluorochrome is in the range of about 0.1 nanoseconds to about 500 nanoseconds.

In one embodiment of the invention, the fluorochrome has a skeletal structure of fluorescein, dansyl, pyrene, rhodamine, dialkylaminonaphthalene, dialkylamnionaphthalenesulfonyl, cyanin, or indolenine.

In one embodiment of the invention, each of the fluorochromes is selected so that the fluorochrome is different from the other fluorochromes in terms of at least one of excitation wavelength, fluorescence wavelength, and lifetime of fluorescence.

According to another aspect of this invention, there is provided a kit for use in a fluorescence polarization method at multiple wavelengths for analyzing two or more different assay-objects in a sample. The kit includes two or more different fluorescent-labeled substances, each being a substance which is capable of specifically binding to respective one of the assay-objects and is covalently bound to a fluorochrome, wherein the fluorochromes of the fluorescent-labeled substances are different from one another.

According to still another aspect of this invention, there is provided a system for use in a fluorescence polarization method at multiple wavelengths for analyzing two or more different assay-objects in a sample. The system includes: (a) two or more different fluorescent-labeled substances, each being a substance which is capable of specifically binding to respective one of the assay-objects and is covalently bound to a fluorochrome, wherein the fluorochromes of the fluorescent-labeled substances are different from one another; and (b) means for measuring the degree of fluorescence polarization.

In the assay system according to the method of the present invention, a change in molecular weight which has taken place in each fluorescent-labeled substance by its binding to an assay-object is measured as a change over time in the molecular orientation. Thus, it is possible to analyze, in a single process, two or more different assay-objects having different molecular weights, by appropriately selecting the types of fluorochromes used as labels in view of the change in molecular weight before and after the binding of fluorochromes.

Thus, the invention described herein makes possible the advantages of (1) providing a fluorescence polarization method at multiple wavelengths for analyzing two or more different assay-objects contained in a sample in one reaction system by measuring a change in the degree of fluorescence polarization for each of the assay-objects; (2) providing a kit for analyzing two or more different assay-objects contained in a sample by using a fluorescence polarization method at multiple wavelengths; and (3) providing a system for analyzing two or more different assay-objects contained in a sample by using a fluorescence polarization method at multiple wavelengths.

These and other advantages of the present invention will become apparent to those skilled in the art upon reading and understanding the following detailed description with reference to the accompanying figure.

DESCRIPTION OF THE PREFERRED EMBODIMENTS

Figure 1:
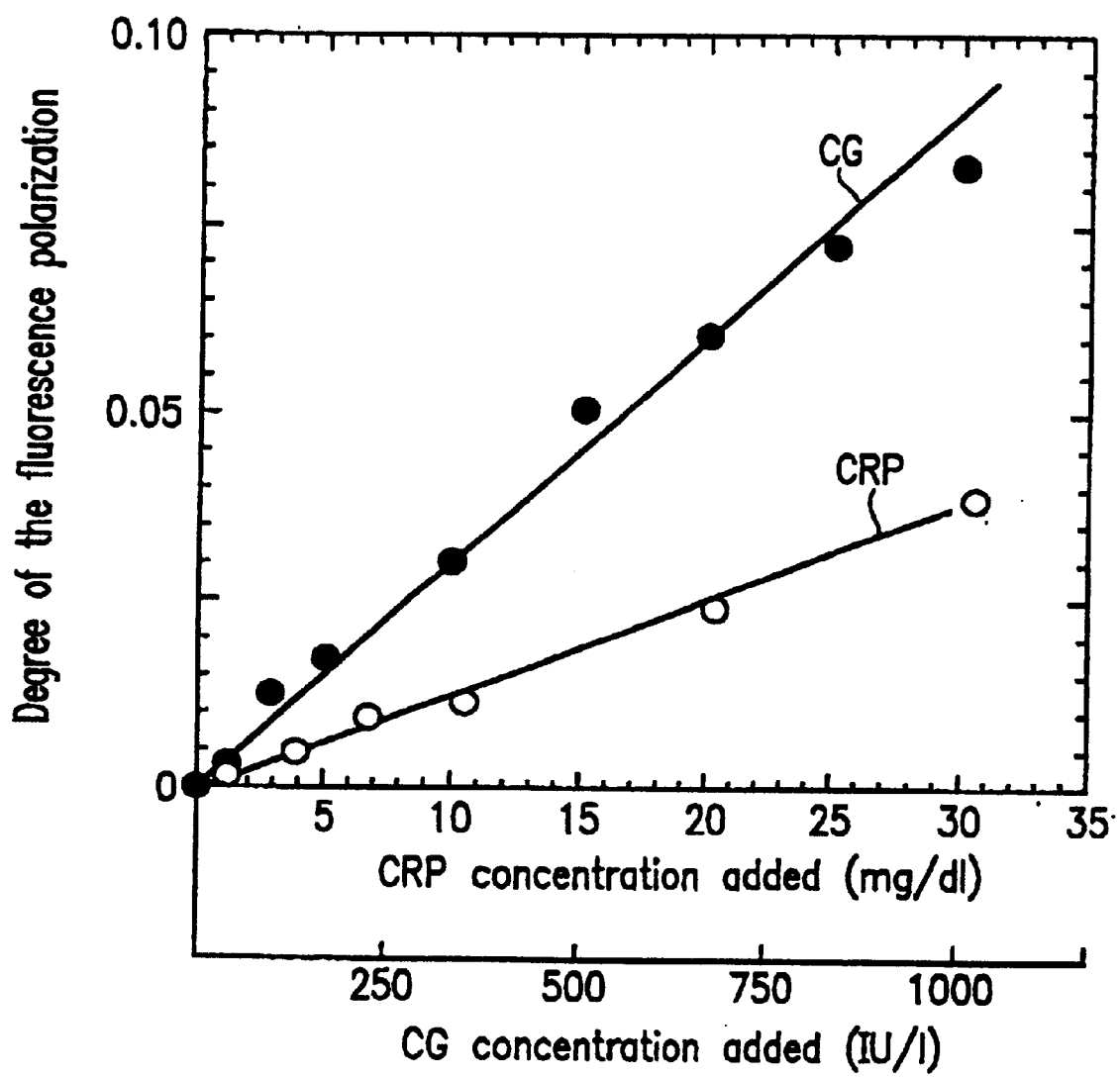
FIG. 1 is a graph showing the results of a simultaneous measurement of CRP and CG using a fluorescence polarization method at multiple wavelengths.

The present invention will be described in greater detail below.

According to the fluorescence polarization method at multiple wavelengths of the present invention, it is possible to analyze, i.e., quantify or detect, two or more different assay-objects in a sample in one reaction system based on the above-described principle of the fluorescence polarization method.

By covalently binding the substance capable of specifically binding to the assay-object (hereinafter, referred to as the "specifically-binding substance"), with a fluorochrome, a fluorescent-labeled substance useful in the method of the present invention is provided.

The specifically-binding substance may be any substance as long as it has a desired binding property with respect to the assay-object, and a functional group which allows for the binding to the fluorochrome. The specifically-binding substance is preferably a protein, and more preferably, a protein which is classified as any of antibodies, antigens, receptors or inhibitors. An antibody is particularly preferred for its broad spectrum of applications. The antibody type includes polyclonal antibodies, a monoclonal antibody, a chimeric antibody, a Fab antibody and a (Fab)2 antibody. Any type of antibody can be applied to the method of the present invention. An antigen is typically used in the case wherein the assay-object is an antibody. A receptor can be used in the case where the assay-object acts as a ligand for the receptor. An inhibitor can be used, for example, in the case where the assay-object is an enzyme.

For the fluorochrome, those having a functional group which can be covalently bound to a functional group of the specifically-binding substance are utilized. The functional group of the specifically-binding substance is typically a primary, secondary or tertiary amino group, a carboxyl group, a thiol group, a phenyl group, a phenol group or a hydroxyl group. Especially, in the case where a protein such as an antibody is used as the specifically-binding substance, in terms of the binding efficiency, a fluorochrome having an activated functional group, e.g., a halogenated sulphonyl group, a succinimidized carboxyl group, or an isothiocyanated primary amino group, is desired.

The number of fluorochrome molecules bound to one molecule of the object to be labeled, i.e., the specifically-binding substance, can be varied arbitrarily. It is preferred in order to increase the detection sensitivity to bind two or more fluorochromes. However, when more fluorochromes than necessary are bound, it may adversely affect a property of the specifically-binding substance. For example, it may reduce the affinity, solubility, or the like, of the antibody. Therefore, the above-described binding number is preferably about 10 or less and, more preferably, about one.

The present invention utilizes different fluorochromes for different assay-objects in order to analyze two or more different assay-objects in one reaction system. The combination of the fluorochromes is preferably selected so that any pair of fluorochromes are different from each other in terms of at least one of excitation wavelength, fluorescence wavelength, and lifetime of fluorescence. In order to simplify the assay procedure, the selected fluorochromes are preferably different from one another in terms of either or both of excitation wavelength and fluorescence wavelength, particularly, excitation wavelength.

When selecting the skeletal structure of the fluorochrome to be used, the excitation wavelength, the fluorescence wavelength, the Stokes shift and the lifetime of the fluorescence are important. Preferably, either or both of the excitation wavelength and the fluorescence wavelength exist in the visible light wavelength range, i.e., 300 nm to 700 nm. Preferably, the difference in wavelength between the excitation wavelength and the fluorescence wavelength, i.e., the Stokes shift, is at least 20 nm or more. The lifetime of the fluorescence (the fluorescence relaxation time) of the fluorochromes is typically selected from the range of about 0.1 nanoseconds to about 1,000 nanoseconds. In another embodiment, the lifetime of the fluorescence may be in the range of about 0.1 nanoseconds to about 500 nanoseconds. In selecting the lifetime of the fluorescence, the change in molecular weight of the fluorescent-labeled substance through the binding to the assay-object is taken into consideration. This is because the degree of polarization of fluorescence emitted from the fluorescent-labeled substance bound to the assay-object in a proportional relationship with the size of the molecule.

Specifically, when the change in the molecular weight is about 5,000 to about 50,000, i.e., when the molecular weight of the assay-object is several thousands to several ten thousands, a fluorochrome having a lifetime of the fluorescence of about 1 to 15 nanoseconds is preferred. Examples of such a fluorochrome include dansyl derivatives and fluorescein. When the change in the molecular weight is about 50,000 to about 500,000, i.e., when the molecular weight of the assay-object is about several ten thousands to several hundred thousands, a fluorochrome having a lifetime of the fluorescence of about 10 nanoseconds to about 150 nanoseconds is preferred. Examples or such a fluorochrome includes dansyl derivatives and pyrene derivatives. When the change in the molecular weight is about 500,000 to about 5,000,000, i.e., when the molecular weight of the assay-object is about several hundred thousands to several millions, a fluorochrome having a lifetime of the fluorescence of about 100 nanoseconds to about 1,000 nanoseconds is preferred. Examples of such a fluorochrome include pyrene derivatives and metal complexes.

From the above-described points of view, preferred examples of fluorochrome include fluorochromes having a skeletal structure of rhodamine, pyrene, fluorescein, dialkylaminonaphthalene, dialkylaminonaphthalenesulfonyl, cyanin, or indolenine. A particularly preferred fluorochrome may be a fluorochrome having a skeletal structure of fluorescein, dansyl or pyrene.

The reaction for forming the covalent bond between the specifically-binding substance and the fluorochrome can be carried out according to conditions well known to those skilled in the art. When the specifically-binding substance has a primary, secondary or tertiary amino group, a carboxyl group, a thiol group, a phenyl group, a phenol group or a hydroxyl group, the covalent bond can be formed by reacting the specifically-binding substance and the fluorochrome having an activated functional group normally at room temperature for several hours. After the completion of the reaction, the unreacted fluorochrome can be easily removed by an ordinary method, e.g., gel filtration or dialysis. The specifically-binding substance and the fluorochrome can be bound directly or can be bound indirectly via a bifunctional linker molecule, or the like.

By using appropriately selected two or more of the above-described fluorescent-labeled substances, two or more different assay-objects in a sample can be analyzed as follows.

The sample containing the two or more different assay-objects and the fluorescent-labeled substances are mixed with each other in a solution so as to measure the degree of fluorescence polarization of the fluorescent-labeled substance in the mixed solution. If necessary, the two or more different fluorescent-labeled substances are mixed in a solution, and the degree of fluorescence polarization of each of the fluorescent-labeled substances in the absence of the assay-object is also measured. Any polarization measurement apparatus can be used for measuring the degree of fluorescence polarization. The measurement is performed at a mild temperature (about 10 degrees centigrade (° C.) to about 40° C.) and, preferably, at a constant temperature.

The measurement of the degree of fluorescence polarization can be performed by measuring the degree after a predetermined time from the mixing of the assay-objects and the fluorescent-labeled substances, or by measuring a change in the degree of fluorescence polarization for a unit of time. By taking a measurement at the time when the binding between each assay-object and the corresponding fluorescent-labeled substance has been completely finished, more reproducible measurement values are obtained. By measuring the change in the degree of fluorescence polarization for a unit of time while the binding reaction between each assay-object and the corresponding fluorescent-labeled substance is in progress, on the other hand, a quicker measurement is possible. For the purpose of quantifying the assay-object contained in the sample, a standard curve is provided through a measurement of the degree of fluorescence polarization using a solution containing a known concentration of the assay-object so as to compare it with the measurement value for the sample.

The sample intended to be used with the method of the present invention is a material including two or more assay-objects desired to be analyzed in any field of art including environmental assay, food control, and medical diagnosis. Exemplary samples for environmental assay include materials collected from soil, a river, the air, or the like. Exemplary samples for food control include an extract from ground meat, and an extract from a chopping board. Exemplary samples for medical diagnosis include body fluids including a blood, a lymph, and a tissue fluid. The sample can be in any form so long as it can be used with the method of the present invention.

The assay-objects of the method of the present invention include, but are not limited to, a biological substance, a microorganism, a virus, a pharmaceutical, an environmental pollutant and an abused drug.

The biological substance refers to any organic or inorganic substance existing in the body of a human or other mammal. Typical examples of the biological substance include a peptide, a protein, a lipid, a saccharide and a nucleic acid. The microorganism includes a bacteria, a fungus and a protozoan. The virus includes a bacterial virus, a plant virus and an animal virus. The pharmaceutical includes any agent used for treating or diagnosing a human or other mammals. Examples of the pharmaceutical include, but are not limited to, digoxin and cyclopoietin. The environmental pollutant includes any substance causing environmental pollution which can be detected from soil, a river, the air, or the like. Examples of the environmental pollutant include, but are not limited to, environmental hormones such as dioxin. The abused drug refers to a drug, intake of which by a human is restricted by law or regulation, and which has been used in violation of the restriction. Examples of the abused drug include, but are not limited to, cocaine, methamphetamine, opium and morphine.

The present invention also provides a kit suitable for use in the above-described method, comprising two or more fluorescent-labeled substances. The fluorescent-labeled substances may be contained in a sealed container individually or in combination. The fluorescent-labeled substance may be provided in various forms such as a dry form, a solution form wherein the substance is dissolved in a buffer solution, or the like. The kit may also include, as necessary, a standard solution containing a known concentration of an assay-object, a diluent, and an instruction manual.

The present invention further provides a system for analyzing two or more different assay-objects, comprising the above-described fluorescent-labeled substances and a fluorescence polarization measurement apparatus. The system may include, as necessary, other substances and apparatuses such as an apparatus for pre-treatment of a sample, a computer for automated analysis of measured data, and the like.

The following examples of the invention are intended to illustrate, but not to limit, the present invention.

EXAMPLES (Example 1)

Hereinbelow, the results of measurements in one reaction system for two different assay-objects: chorionic gonoadotropin (CG: molecular weight of about 37,000) and C-reactive protein (CRP: molecular weight of about 120,000) according to the present invention will be described. F-4000 manufactured by Hitachi Ltd. was used as an apparatus for measuring the degree of fluorescence polarization.

1. Preparation of Dansyl-Labeled Anti-CG Polyclonal Antibodies

A set of dansyl-labeled anti-CG polyclonal antibodies was prepared as described below, using anti-CG polyclonal antibodies (obtained from Bio Reactive) and dansyl chloride (obtained from Wako Pure Chemical Industries, Ltd.).

A solution (about 1000 $\mu$l) containing about 2.0 mg/ml of the anti-CG polyclonal antibodies in a phosphate-buffered saline (PBS) (pH: about 7.4) was mixed with a solution (about 20 $\mu$l) containing about 1.00 mg/ml of dansyl chloride (10-fold amount of antibodies) dissolved in acetone. The mixed solution was reacted to about 4° C. for about 24 hours while stirring. The reacted solution was subjected to Sephadex G-25 gel filtration column (Pharmacia) (size: about 10×60 mm, flow rate: about 2 ml/min). Unreacted dansyl chloride was removed, and fractions containing the dansyl-labeled anti-CG polyclonal antibodies were collected.

The collected fractions were used to evaluate the labeling amount and the fluorescence property of the prepared dansyl-labeled anti-CG polyclonal antibodies. The labeling amount was measured using an ultraviolet/visible spectrometer (manufactured by Shimadzu Corp., UV-1600PC), confirming labeling of about 0.2 dansyl per one molecule of the anti-CG polyclonal antibodies. The fluorescence property was measured using a fluorescence spectrometer (manufactured by Shimadazu Corp., RF-5300PC), confirming that the fluorescence property of dansyl bound to the anti-CG polyclonal antibodies was such that the excitation wavelength was about 335 nm, the resulting fluorescence wavelength was about 520 nm, and the lifetime of the fluorescence was about 12 nanoseconds.

2. Preparation of Pyrene-Labeled Anti-CRP Polyclonal Antibodies

A set of pyrene-labeled anti-CRP polyclonal antibodies was prepared as described below, using an anti-CRP polyclonal antibodies (obtained from Bio Reactive) and succinimidylpyrenebutyrate (SPB) (obtained from Molecular Probes, Inc.).

A solution (about 1000 $\mu$l) containing about 2.0 mg/ml of the anti-CRP polyclonal antibodies in a phosphate-buffered saline (PBS) (pH: about 7.4) was mixed with a solution (about 20 $\mu$l) containing about 1.29 mg/ml of SPB (5-fold amount of antibodies) dissolved in dimethyl sulfoxide (DMSO). The mixed solution was reacted at room temperature for about 4 hours while stirring. The reacted solution was subjected to Sephadex G-25 gel filtration column (Pharmacia) (size: about 10×60 mm, flow rate: about 2 ml/min). Unreacted SPB was removed, and fractions containing the pyrene-labeled anti-CRP polyclonal antibodies were collected.

The collected fractions were used to evaluate the labeling amount and the fluorescence property of the prepared pyrene-labeled anti-CRP polyclonal antibodies. The labeling amount was measured using an ultraviolet/visible spectrometer (manufactured by Shimadzu Corp., UV-1600PC), confirming labeling of about 1.1 pyrenes per one molecule of the anti-CRP polyclonal antibodies. The fluorescence property was measured using a fluorescence spectrometer (manufactured by Shimadzu Corp., RF-5300PC), finding that the fluorescence property of pyrene bound to the anti-CRP polyclonal antibodies was such that the excitation wavelength was about 330 nm, the resulting fluorescence wavelengths were about 373 nm and about 397 nm, and the lifetime of the fluorescence was about 60 nanoseconds. Since the fluorescence intensity was greater at about 397 nm, as the measurement conditions to be used with the fluorescence polarization method, it was determined to utilize the excitation wavelength of about 330 nm and the fluorescence wavelength of about 397 nm.

3. Simultaneous Measurement of CRP and CG

The amounts of CRP and CG in samples were determined by measuring the fluorescence polarity using the dansyl-labeled anti-CG polyclonal antibodies prepared in Example 1.1 and the pyrene-labeled anti-CRP polyclonal antibodies prepared in Example 1.2.

A solution (about 350 $\mu$l) containing the pyrene-labeled anti-CRP polyclonal antibodies at about 400 $\mu$g/ml was mixed with another solution (about 350 $\mu$l) containing the dansyl-labeled anti-CG polyclonal antibodies at about 400 $\mu$g/ml. The mixed solution was placed into a cuvette (about 5×5 mm) so as to measure the degree of fluorescence polarization. The measurement conditions for the pyrene-labeled anti-CRP polyclonal antibodies were as follows: a measurement temperature of about 35° C., an excitation wavelength of about 330 nm, a fluorescence wavelength of about 397 nm and a G factor of about 0.942. The measurement conditions for the dansyl-labeled anti-CG polyclonal antibodies were as follows: a measurement temperature of about 35° C. an excitation wavelength of about 330 nm, a fluorescence wavelength of about 520 nm and a G factor of about 1.320.

Solutions respectively containing 0, 0.1, 0.2, 0.3, 0.4, 0.5, 1, 4, 7, 10, 20, 30, and 50 mg/dl of CRP (obtained from O.E.M. Concepts, Inc.), and other solutions respectively containing 0, 50, 100, 200, 300, 500, 600, 800, and 1000 IU/l of CG (obtained from National of Health Sciences, Japan) were prepared. The above-described mixed solution of the labeled antibodies (about 700 $\mu$l) was mixed with each concentration of the CRP solution (about 60 $\mu$l) and each concentration of the CG solution (about 60 $\mu$l). The mixture was stirred at about 35° C. and for about 0.5 minute. Then, the degree of fluorescence polarization for CRP and that for CG were measured under the above-described measurement conditions and for about 0.5 minutes, thereby observing changes thereof. The results are shown in FIG. 1. The horizontal axis indicates the concentration of each assay-object as added before mixed with the mixed solution of the labeled antibodies.

It was confirmed that CRP and CG can be respectively measured in a mixed solution containing CRP and CG. The change in the degree of fluorescence polarization for CRP was shown to be linear up to a concentration of about 30 mg/dl, whereas that for CG was shown to be linear up to a concentration of about 1000 IU/L.

(Example 2)

Hereinbelow, the results of measurements in one reaction system for two different assay-objects: Amyloid A (molecular weight of about 85,000) and C-reactive protein (CRP; molecular weight of about 120,000) according to the present invention will be described. F-4000 manufactured by Hitachi Ltd. was used as an apparatus for measuring the degree of fluorescence polarization.

1. Preparation of Dansyl-Labeled Anti-Amyloid A Polyclonal Antibodies

A set of dansyl-labeled anti-Amyloid A Polyclonal Antibodies

A set of dansyl-labeled anti-Amyloid A polyclonal antibodies was prepared as described below, using anti-Amyloid A polyclonal antibodies (obtained from Bio Reactive) and dansyl chloride (obtained from Wako Pure Chemical Industries, Ltd.).

A solution (about 1000 µl) containing about 2.0 mg/ml of the anti-Amyloid A polyclonal antibodies in a phosphate-buffered saline (PBS) (pH: about 7.4) was mixed with a solution (about 20 µl) containing about 1.00 mg/ml of dansyl chloride (10-fold amount of antibodies) dissolved in acetone. The mixed solution was reacted at about 4° C. for about 24 hours while stirring. The reacted solution was subjected to Sephadex G-25 gel filtration column (Pharmacia) (size: about 10×60 mm, flow rate: about 2 ml/min). Unreacted dansyl chloride was removed, and fractions containing the dansyl-labeled anti-Amyloid A polyclonal antibodies were collected.

The collected fractions were used to evaluate the labeling amount and the fluorescence property of the prepared dansyl-labeled anti-Amyloid A polyclonal antibodies. The labeling amount was measured using an ultraviolet/visible spectrometer (manufactured by Shimadzu Corp., UV-1600PC), confirming labeling of about 0.26 dansyl per one molecule of the anti-Amyloid A polyclonal antibodies. The fluorescence property was measured using a fluorescence spectrometer (manufactured by Shimadzu Corp., RF-5300PC), confirming that the fluorescence property of dansyl bound to the a set of anti-Amyloid A polyclonal antibodies was such that the excitation wavelength was about 335 nm, the resulting fluorescence wavelength was about 520 nm, and the lifetime of the fluorescence was about 12 nanoseconds.

2. Simultaneous Measurement of CRP and Amyloid A

The amounts of CRP and Amyloid A in samples were determined by measuring the fluorescence polarity using the set of dansyl-labeled anti-Amyloid A polyclonal antibodies prepared in Example 2.1 and the set of pyrene-labeled anti-CRP polyclonal antibodies prepared in Example 1.2.

A solution (about 350 µl) containing the pyrene-labeled anti-CRP polyclonal antibodies at about 400 µg/ml was mixed with another solution (about 350 µl) containing the dansyl-labeled anti-Amyloid A polyclonal antibodies at about 400 µg/ml. The mixed solution was placed into a cuvette (about 5×5 mm) so as to measure the degree of fluorescence polarization. The measurement conditions for the pyrene-labeled anti-CRP polyclonal antibodies were as follows: a measurement temperature of about 35° C., an excitation wavelength of about 330 nm, a fluorescence wavelength of about 397 nm and a G factor of about 0.942. The measurement conditions for the dansyl-labeled anti-Amyloid A polyclonal antibodies were as follows: a measurement temperature of about 35° C., an excitation wavelength of about 330 nm, a fluorescence wavelength of about 520 nm and a G factor of about 1.320.

Figure 2:
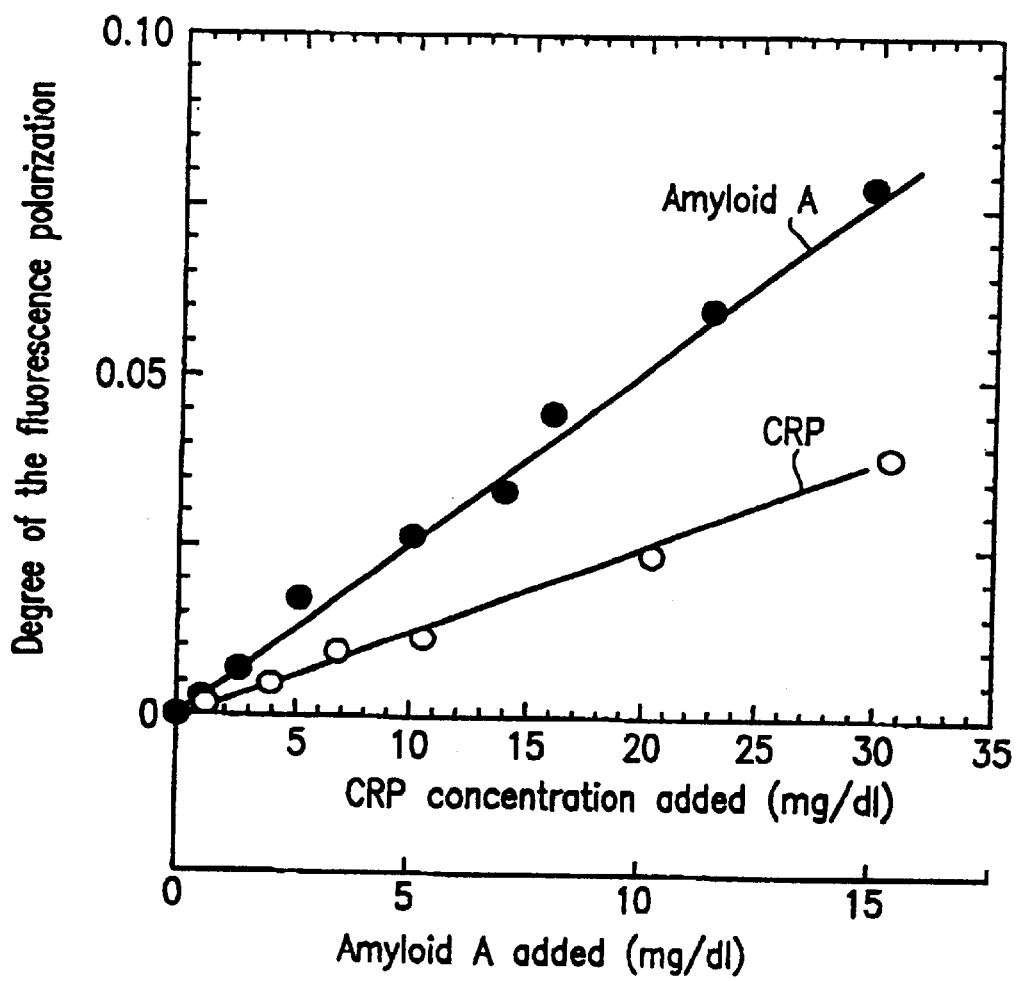
FIG. 2 is a graph showing the results of a simultaneous measurement of CRP and Amyloid A using a fluorescence polarization method at multiple wavelengths.

Solutions respectively containing 0, 0.1, 0.2, 0.3, 0.4, 0.5, 1, 4, 7, 10, 20, 30, and 50 mg/dl of CRP (obtained from O.E.M. Concepts, Inc.), and other solutions respectively containing 0, 1, 2, 3, 5, 7, 8, 12, 15, and 20 mg/dl of Amyloid A (obtained from COSMO BIO CO., Ltd.) were prepared. The above-described mixed solution of the labeled antibodies (about 700 µl) was mixed with each concentration of the CRP solution (about 60 µl) and each concentration of the Amyloid A solution (about 60 µl). The mixture was stirred at about 35° C. and for about 0.5 minute. Then, the degree of fluorescence polarization for CRP and that for Amyloid A were measured under the above-described measurement conditions and for about 0.5 minutes, thereby observing changes thereof. The results are shown in FIG. 2. The horizontal axis indicates the concentrations of each assay-objects as added before mixed with the solution of the labeled antibodies.

It was confirmed that CRP and Amyloid A can be respectively measured in a mixed solution containing CRP and Amyloid A. The change in the degree of fluorescence polarization for CRP showed to be linear up to a concentration of about 30 mg/dl, whereas that for Amyloid A showed to be linear up to a concentration of about 15 mg/dl.

The method of the present invention provides a fluorescence polarization method at multiple wavelengths which allows for an easy, quick and high-accuracy analysis of two or more different assay-objects contained in a sample in one reaction system.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A fluorescence polarization method at multiple wavelengths for analyzing two or more different assay-objects in a sample, the method comprising the steps of:
   (a) providing two or more different fluorescent-labeled substances, each being a substance which is capable of specifically binding to respective one of the assay-objects and is covalently bound to a fluorochrome, wherein the fluorochromes of the fluorescent-labeled substances are different from one another, wherein the fluorescence lifetime of each fluorochrome is selected based on the change in molecular weight of the fluorescent-labeled substance resulting from the binding to the assay-object, and wherein each of the fluorochromes is selected so that the fluorochrome is different from the other fluorochromes in terms of excitation wavelength and/or fluorescence wavelength;
   (b) allowing the fluorescent-labeled substances to bind to the two or more different assay-objects respectively; and
   (c) measuring a change in the degree of fluorescence polarization which has taken place in each of the fluorescent-labeled substances by its binding to one of the assay-objects.

2. A kit for use in a fluorescence polarization method at multiple wavelengths for analyzing two or more different assay-objects in a sample, the kit comprising two or more different fluorescent-labeled substances, each being a substance which is capable of specifically binding to respective one of the assay-objects and is covalently bound to a fluorochrome, wherein the fluorochromes of the fluorescent-labeled substances are different from one another, wherein the fluorescence lifetime of each fluorochrome is selected based on the change in molecular weight of the fluorescent-labeled substance resulting from the binding to the assay-object, and wherein each of the fluorochromes is selected so that the fluorochrome is different from the other fluorochromes in terms of excitation wavelength and/or fluorescence wavelength.

3. A system for use in a fluorescence polarization method at multiple wavelengths for analyzing two or more different assay-objects in a sample, the system comprising:
   (a) two or more different fluorescent-labeled substances, each being a substance which is capable of specifically binding to respective one of the assay-objects and is directly covalently bound to a fluorochrome, wherein the fluorochromes of the fluorescent-labeled substances are different from one another, wherein the fluorescence lifetime of each fluorochrome is selected based on the change in molecular weight of the fluorescent-labeled substance resulting from the binding to the assay-object, and wherein each of the fluorochromes is selected so that the fluorochrome is different from the other fluorochromes in terms of excitation wavelength and/or fluorescence wavelength; and (b) means for measuring the degree of fluorescence polarization.

4. A fluorescence polarization method at multiple wavelengths according to claim 1, wherein each of the two or more different assay-objects is independently a biological substance, a microorganism, a virus, a pharmaceutical, an environmental pollutant, or an abused drug.

5. A fluorescence polarization method at multiple wavelengths according to claim 1, wherein the fluorochrome has a functional group which is capable of binding to a primary, secondary, or tertiary amino group, a carboxyl group, a thiol group, a phenyl group, a phenol group, or a hydroxyl group.

6. A fluorescence polarization method at multiple wavelengths according to claim 1, wherein a lifetime of fluorescence of the fluorochrome is in the range of about 0.1 nanoseconds to about 500 nanoseconds.

7. A fluorescence polarization method at multiple wavelengths according to claim 1, wherein the fluorochrome has a skeletal structure of fluorescein, dansyl, pyrene, rhodamine, dialkylaminonaphthalene, dialkylaminonaphthalenesulfonyl, cyanin, or indolenine.

8. A fluorescence polarization method at multiple wavelengths according to claim 1, wherein each of the fluorochromes is different from the other fluorochromes in terms of lifetime of fluorescence.

9. A fluorescence polarization method at multiple wavelengths according to claim 1, wherein each of the fluorochromes is selected so that when the change in molecular weight of the fluorescent-labeled substance resulting from the binding to the assay-object is about 5,000 to 50,000, the lifetime of the fluorescence of each fluorochrome is about 1 nanosecond to about 15 nanoseconds, and when the change is about 50,000 to 500,000, the lifetime of the fluorescence of each fluorochrome is about 10 nanoseconds to about 150 nanoseconds, and when the change is about 500,000 to 5,000,000, the lifetime of the fluorescence of each fluorochrome is about 100 nanoseconds to about 1,000 nanoseconds.

10. A kit according to claim 2, wherein each of the fluorochromes is selected so that when the change in molecular weight of the fluorescent-labeled substance resulting from the binding to the assay-object is about 5,000 to 50,000, the lifetime of the fluorescence of each fluorochrome is about 1 nanosecond to about 15 nanoseconds, and when the change is about 50,000 to 500,000, the lifetime of the fluorescence of each fluorochrome is about 10 nanoseconds to about 150 nanoseconds, and when the change is about 500,000 to 5,000,000, the lifetime of the fluorescence of each fluorochrome is about 100 nanoseconds to about 1,000 nanoseconds.

11. A system according to claim 3, wherein each of the fluorochromes is selected so that when the change in molecular weight of the fluorescent-labeled substance resulting from the binding to the assay-object is about 5,000 to 50,000, the lifetime of the fluorescence of each fluorochrome is about 1 nanosecond to about 15 nanoseconds, and when the change is about 50,000 to 500,000, the lifetime of the fluorescence of each fluorochrome is about 10 nanoseconds to about 150 nanoseconds, and when the change is about 500,000 to 5,000,000, the lifetime of the fluorescence of each fluorochrome is about 100 nanoseconds to about 1,000 nanoseconds.

12. A fluorescence polarization method at multiple wavelengths according to claim 1, wherein each of the fluorochromes is selected so that the lifetime of the fluorescence of each fluorochrome is about 0.1 nanosecond to 1 nanosecond.

13. A kit according to claim 2, wherein each of the fluorochromes is selected so that the lifetime of the fluorescence of each fluorochrome is about 0.1 nanosecond to 1 nanosecond.

14. A system according to claim 3, wherein each of the fluorochromes is selected so that the lifetime of the fluorescence of each fluorochrome is about 0.1 nanosecond to 1 nanosecond.

* * * * *